(12) United States Patent
Auguste et al.

(10) Patent No.: US 7,029,662 B2
(45) Date of Patent: *Apr. 18, 2006

(54) MASCARA COMPRISING SOLID PARTICLES

(75) Inventors: Frédéric Auguste, Chevilly-Larue (FR); Florence Tournilhac, Paris (FR)

(73) Assignee: L'Oreal, Paris (FR)

( * ) Notice: Subject to any disclaimer, the term of this patent is extended or adjusted under 35 U.S.C. 154(b) by 125 days.

This patent is subject to a terminal disclaimer.

(21) Appl. No.: 10/195,419

(22) Filed: Jul. 16, 2002

(65) Prior Publication Data

US 2003/0059388 A1 Mar. 27, 2003

Related U.S. Application Data

(60) Provisional application No. 60/306,442, filed on Jul. 20, 2001.

(30) Foreign Application Priority Data

Jul. 16, 2001 (FR) .................................. 01 09505

(51) Int. Cl.
*A61K 7/02* (2006.01)
(52) U.S. Cl. ..................... 424/70.7; 424/401
(58) Field of Classification Search ................ 424/401, 424/70.7
See application file for complete search history.

(56) References Cited

U.S. PATENT DOCUMENTS

| | | | |
|---|---|---|---|
| 3,937,811 A | 2/1976 | Papantoniou et al. | |
| 5,389,363 A * | 2/1995 | Snyder et al. ............. | 424/70.7 |
| 5,849,278 A | 12/1998 | Piot et al. | |
| 5,851,517 A | 12/1998 | Mougin et al. | |
| 5,858,338 A | 1/1999 | Piot et al. | |
| 5,945,095 A | 8/1999 | Mougin et al. | |
| 5,961,989 A | 10/1999 | Mougin et al. | |
| 6,254,877 B1 | 7/2001 | De La Poterie et al. | |
| 6,274,131 B1 | 8/2001 | Piot et al. | |
| 6,491,931 B1 * | 12/2002 | Collin ........................ | 424/401 |
| 6,682,748 B1 * | 1/2004 | De La Poterie et al. .... | 424/401 |
| 2001/0006665 A1 | 7/2001 | Auguste | |
| 2002/0085986 A1 | 7/2002 | De La Poterie et al. | |
| 2004/0009201 A1 | 1/2004 | Collin et al. | |

FOREIGN PATENT DOCUMENTS

WO WO 98/23251 8/1998

OTHER PUBLICATIONS

Kirk-Othmer, "Encyclopedia of Chemical Technology," Third Edition, vol. 22, John Wiley & Sons, 1983, pp. 333-433.
English language Derwent Abstract of EP 0 847 752, Jun. 17, 1998.
English language Derwent Abstract of EP 0 923 928, Jun. 23, 1999.
English language Derwent Abstract of EP 1 048 282, Nov. 2, 2000.
English language Derwent Abstract of EP 1 064 920, Jan. 3, 2001.
English language Derwent Abstract of EP 1 082 953, Mar. 14, 2001.
English language Derwent Abstract of FR 2 792 190, Oct. 20, 2000.
English language Derwent Abstract of FR 2 794 970, Dec. 22, 2000.
French Search Report for FR 01 09502 dated Apr. 22, 2002, Examiner D. Angiolini.
French Search Reportfor FR 01 09503 dated Apr. 23, 2002, Examiner G. Willekens.

* cited by examiner

*Primary Examiner*—Jyothsna A. Venkat
(74) *Attorney, Agent, or Firm*—Finnegan, Henderson, Farabow, Garrett & Dunner, L.L.P.

(57) ABSTRACT

A composition for coating keratinous fibers, such as eyelashes or hair, comprising a wax-in-water dispersion comprising, in a cosmetically acceptable medium, a nonvolatile fraction comprising: at least one polymer capable of adhering to the keratinous fibers, particles which are solid at 25° C. of a wax chosen from waxes having a melting point of less than 77° C. and a hardness greater than or equal to 6.5 MPa. The solid particles are present in the composition in an amount such that the volume fraction of the solid particles of wax is greater than or equal to 50% of the total volume of the nonvolatile fraction of the composition. The composition can make it possible to obtain good curling of keratinous fibers, such as eyelashes.

99 Claims, No Drawings

MASCARA COMPRISING SOLID PARTICLES

This application claims priority to U.S. Provisional Application No. 60/306,442, filed Jul. 20, 2001.

One subject of the present invention is a cosmetic composition for coating keratinous fibers such as eyelashes or hair, comprising solid particles and at least one adherent polymer. The present invention also relates to methods for curling keratinous fibers with the cosmetic compositions described herein. The composition can be applied to substantially longitudinal keratinous fibers of humans, such as eyelashes or hair or alternatively false eyelashes or postiches such as wigs. The composition can also be used for coating the eyelashes.

The composition may be a make-up composition, also called mascara, a composition to be applied over a make up, also called top coat, or alternatively a composition for treating keratinous fibers, such as eyelashes. In one embodiment, the composition is a mascara.

The present invention can provide a composition for coating eyelashes leading, after application, to a coat, which can confer good curling of the eyelashes.

The inventors have discovered that such a coating of the eyelashes could be obtained using particular solid particles combined with an adherent polymer.

One aspect of the invention provides a composition for coating keratinous fibers, such as eyelashes, comprising a wax-in-water dispersion comprising, in a cosmetically acceptable aqueous medium, a nonvolatile fraction comprising:

at least one polymer capable of adhering to the keratinous fibers, first particles which are solid at 25° C. comprising a first material comprising at least one wax having a melting point of less than 77° C. and a hardness greater than or equal to 6.5 MPa, and optionally second solid particles comprising a second material different from the first material, the second solid particles not being capable of coalescing at a temperature of less than or equal to 40° C., wherein the first solid particles and, where appropriate, the second solid particles being present in the composition in an amount such that the volume fraction of the first solid particles and, where appropriate, of the second solid particles is greater than or equal to 50% of the total volume of the nonvolatile fraction of the composition, and, where appropriate, the volume fraction of the first solid particles is greater than or equal to 25% of the total volume of the first solid particles and of the second solid particles.

Another aspect of the invention provides a mascara comprising a composition as described herein.

Another aspect of the invention provides a method of applying make-up to or for a nontherapeutic treatment of keratinous fibers, such as eyelashes, comprising applying to the keratinous fibers a composition as described herein.

Another aspect of the invention provides a method for curling keratinous fibers, such as eyelashes, comprising applying to the keratinous fibers in an amount effective to curl the keratinous fibers, a composition as described herein.

Another aspect of the invention provides a method for improving the curling capability of a composition for curling keratinous fibers, the composition comprising a wax-in-water dispersion comprising, in a cosmetically acceptable aqueous medium, a nonvolatile fraction comprising at least one polymer capable of adhering to keratinous fibers. The method comprises adding to the non-volatile fraction:

first particles which are solid at 25° C. comprising a first material comprising at least one wax having a melting point of less than 77° C. and a hardness of greater than or equal to 6.5 MPa, and optionally second solid particles comprising a second material different from the first material, the second solid particles not being capable of coalescing at a temperature of less than or equal to 40° C., wherein the first solid particles and, where appropriate, the second solid particles are present in the composition in an amount such that the volume fraction of the first solid particles and, where appropriate, of the second solid particles is greater than or equal to 50% of the total volume of the nonvolatile fraction of the composition, and, where appropriate, the volume fraction of the first solid particles is greater than or equal to 25% of the total volume of the first solid particles and of the second solid particles.

The expression "solid particles" is understood to mean particles which are in the solid state at 25° C. and at atmospheric pressure.

The expression "nonvolatile fraction of the composition" is understood to mean the combination of the constituents present in the composition which are not volatile. The expression "volatile compound" is understood to mean a compound which, taken in isolation, has a non-zero vapor pressure, at room temperature (25° C.) and atmospheric pressure, ranging from $10^{-2}$ to 300 mmHg (1.33 Pa to 40 000 Pa) such as pressures greater than 0.3 mmHg (40 Pa).

In one embodiment, the nonvolatile fraction of the composition can correspond to the mixture of the constituents remaining on the eyelashes after drying of the mascara, containing the composition, applied to the eyelashes.

In one embodiment, to obtain good curling of the eyelashes, the composition according to the invention comprises solid particles, called first solid particles, comprising at least one wax, alternatively called a "hard wax", having a melting point of less than 77° C. and a hardness of greater than or equal to 6.5 MPa.

The expression "wax" is understood to mean, within the general context of the present invention, a lipophilic fatty compound, which is solid at room temperature (25° C.) and atmospheric pressure (760 mmHg, that is $10^5$ Pa), with a reversible solid/liquid change of state, having a melting point greater than 30° C. and which may be up to 200° C., such as a melting point up to 120° C. (the wax forming the first solid particles described above corresponds to a particular wax having the characteristics of melting point and hardness mentioned).

By heating the wax to its melting point, it is possible to make it miscible with oils and to form a microscopically homogeneous mixture, but on bringing the temperature of the mixture back to room temperature, recrystallization of the wax in the oils of the mixture is obtained.

The melting point values can correspond, according to the invention, to the peak of melting measured using a differential scanning calorimeter (DSC), for example the calorimeter sold under the name DSC 30 by the company METLER, with a rise in temperature of 5 or 10° C. per minute.

The hard wax can have a melting point of less than 60° C., such as a melting point ranging from 30° C. to 59° C., further such as ranging from 35° C. to 59° C., and even further ranging from 40° C. to 50° C.

The hard wax may have a hardness ranging from 6.5 MPa to 20 MPa, such as a hardness ranging from 6.5 to 15 MPa, further such as ranging from 6.5 to 12 MPa, even further ranging from 9.7 to 20 MPa, further still ranging from 9.7 to 15 MPa, and even further ranging from 9.7 to 12 to MPa.

In one embodiment, the hardness of the wax is determined by measuring the compression force measured at 20° C. using a texturometer sold under the name TA-XT2i by the company RHEO, equipped with a stainless steel cylinder having a diameter of 2 mm, moving at the measuring speed of 0.1 mm/s, and penetrating into the wax at a penetration depth of 0.3 mm. To measure the hardness, the wax is melted at a temperature equal to the melting point of the wax +20° C. The molten wax is poured into a container having a diameter of 30 mm and a depth of 20 mm. The wax is recrystallized at room temperature (25° C.) for 24 hours, and then the wax is stored for at least 1 hour at 20° C. before carrying out the measurement of hardness. The value of the hardness is the measured compacting force divided by the surface area of the texturometer cylinder in contact with the wax.

Representative hard waxes include Candelilla wax, hydrogenated jojoba wax, sumac wax, ceresin, octacosanyl stearate, tetracontanyl stearate, Shellac wax, behenyl fumarate, di(1,1,1-trimethylolpropane) tetrastearate sold under the name "HEST 2T-4S" by the company HETERENE, di(1,1,1-trimethylolpropane) tetrabehenate sold under the name HEST 2T-4B by the company HETERENE, and ozokerites such as that sold under the name "OZOKERITE WAX SP 1020 P" by the company STRAHL & PITSCH.

Other exemplary waxes include waxes obtained by hydrogenation of olive oil esterified with stearyl alcohol, sold under the name "PHYTOWAX Olive 18 L 57" or alternatively the waxes obtained by hydrogenation of castor oil esterified with cetyl alcohol, sold under the name "PHYTOWAX ricin 16L64 and 22L73" by the company SOPHIM. Such waxes are described in application FR-A-2792190.

The hard wax may be chosen from olive wax obtained by hydrogenation of olive oil esterified with stearyl alcohol, sold under the name PHYTOWAX Olive 18 L 57 by the company SOPHIM and di(1,1,1-trimethylolpropane) tetrastearate.

In one embodiment, the said first particles may have a mean size ranging from 50 nm to 50 µm, such as from 100 nm to 10 µm, as measured by methods known to those skilled in the art.

In one embodiment, the first particles may be present in the composition in an amount ranging from 1.25% to 50% by weight, relative to the total weight of the composition, such as an amount ranging from 5% to 40% by weight, and further such as an amount ranging from 10% to 25% by weight.

The composition according to the invention may comprise, in addition to the first solid particles described above, other solid particles, called second particles, different from the first solid particles.

In one embodiment, the second particles correspond to the particles which are solid at 25° C. of any material, different from the first particles, remaining in the form of individualized particles, or optionally of particles stuck together but which retain, in this case, their individual particle state (these particles stuck together are not coalesced at a temperature of less than or equal to 40° C.).

In one embodiment, the second solid particles may comprise particles chosen from:

particles which are solid at 25° C., called second primary solid particles, comprising a first material chosen from crystalline and semicrystalline materials which are solid at room temperature (25° C.) exhibiting at least one of a first order phase transition, a melting transition and a combustion transition, greater than 100° C.;

and/or particles which are solid at 25° C., called second secondary solid particles, comprising at least one amorphous material having a glass transition temperature of greater than or equal to 60° C., and/or other particles which are solid at 25° C., called second tertiary solid particles, different from the said second primary and secondary particles described above and mixtures thereof.

The second primary solid particles are solid particles comprising a material, called a first material, which is crystalline or semicrystalline and which is solid at room temperature (25° C.) having at least one of a first order phase transition, a melting transition, and a combustion transition, greater than 100° C., such as greater than 120° C. or greater than 150° C.

The melting or combustion temperature of the first material may be measured according to the ASTM E794-98 standard.

The expression "semicrystalline material" is understood to mean within the context of the invention, a material, such as a polymer, comprising a crystallizable part and an amorphous part exhibiting a reversible first order phase transition temperature, or a melting point (solid-liquid transition).

In one embodiment, the crystalline or semicrystalline material exhibits a Vickers hardness greater than or equal to 10, such as a hardness ranging from 10 to 7,500, further such as greater than or equal to 200, even further such as ranging from 200 to 7,500, and further still such as greater than or equal to 400, and even further ranging from 400 to 7,500.

The VICKERS hardness (HV) can be determined by applying to the material a penetrometer in the form of a square-base pyramid, using a load P. The mean size of a diagonal of the square impression obtained with the penetrometer can then be measured.

The VICKERS hardness (HV) can then be calculated by the relationship:

$$HV = \frac{1854.4 \times P}{d^2} \quad \begin{array}{l} d = \text{mean diagonal in } \mu m \\ P = \text{load applied in g} \end{array}$$

The measurement of the VICKERS hardness may be carried out using the microdurometer M 400 g 2 from the company LECO.

The first material of the said second primary particles may be an inorganic material which may be chosen from silica, glass, diamond, copper, boron nitride, ceramics, micas, metal oxides, for example, iron oxides such as black iron oxide, red iron oxide, yellow iron oxide, titanium oxides, alumina, and polymer such as a polyamide, for example nylon, and mixtures thereof.

The said second primary particles may be solid particles, or alternatively hollow particles. For example, there may be used the hollow silica sold under the name "SUNSIL-130" by the company SUNJIN CHEMICAL.

In one embodiment, the said second primary particles are formed of the said first material defined above.

In one embodiment, the said second primary solid particles comprise, at least two different first materials. This is, for example, the case of micas coated with titanium oxide or with iron oxide.

In one embodiment, the said second primary particles comprise at least the said first material, and at least an additional material, different from the said first material, the said first material forming the surface of the said first particles. For these solid particles, the said first material having the characteristics described above, exists at the surface of the said second primary solid particles, the latter comprising an additional material coated with the first material.

In embodiment, the said second primary solid particles may have a mean size ranging from 5 nm to 50 µm, such as from 20 nm to 50 µm, as measured by methods known to those skilled in the art.

The second secondary solid particles may comprise at least one amorphous material, such as a polymer, having a glass transition temperature greater than or equal to 60° C., such as a glass transition temperature ranging from 60° C. to 800° C., further such as greater than or equal to 80° C., such as ranging from 80° C. to 700° C., further such as greater than or equal to 100° C., and even further ranging from 100° C. to 500° C. The glass transition temperature may be measured by DSC (Differential Scanning Calorimetry) according to the ASTM D3418-97 standard.

As the at least one amorphous material, there may be used a polymer which is nonfilm-forming at a temperature of less than or equal to 40° C. and which has a glass transition temperature as described above.

The expression "nonfilm-forming polymer" is understood to mean a polymer which is not capable of forming, on its own or in the presence of a film-forming aid, a continuous film which is adherent to a support, in particular to keratinous fibers, at a temperature of less than or equal to 40° C.

The expression "film-forming aid" is understood to mean plasticizing agents and coalescing agents known to persons skilled in the art for promoting film formation by polymers.

As amorphous polymer having a glass transition temperature of greater than or equal to 60° C., there may be used free-radical polymers or polycondensates having this defined glass transition temperature.

As free-radical polymer, there may be mentioned:

polymers of ethylene, such as of cycloethylene and of naphthylethylene;

polymers of propylene, such as of hexafluoropropylene;

acrylic polymers, such as of acrylic acid, of dimethyladamanthyl acrylate, and of chloroacrylate;

polymers of acrylamide;

polymers of (meth)acrylonitrile;

polymers of acetylstyrene, of carboxystyrene, and of chloromethylstyrene.

As representative polycondensates, there may be mentioned polycarbonates, polyurethanes, polyesters, polyamides, polysulphones, polysulphonamides and carbohydrates such as amylose triacetate.

The second secondary solid particles may be solid particles or hollow particles.

In one embodiment, the second secondary solid particles comprise the at least one amorphous material described above.

According to a second embodiment, the second secondary solid particles comprise at least a first amorphous material and at least one additional material, different from the first amorphous material, the said first amorphous material forming the surface, or the crust, of the said second secondary solid particles and the additional material forming the inside, or the core, of the said second secondary solid particles.

The additional material may be, for example, an additional polymer having a glass transition temperature of less than 60° C., such as less than 45° C.

The second secondary solid particles may be, for example, core-shell particles of polymers comprising an outer part, such as a crust, comprising the at least one first amorphous material having a glass transition temperature of greater than or equal to 60° C., and comprising an inner part, such as a core, comprising the additional polymer having a glass transition temperature of less than 60° C.

In one embodiment, the content of the first amorphous material in the second secondary solid particles is such that the volume fraction of the first material is greater than or equal to 10%, such as a volume fraction greater than or equal to 30%, by volume of the total volume of the second secondary solid particles.

The second primary solid particles may have a mean size ranging from 10 nm to 50 µm, such as a mean size ranging from 20 nm to 1 µm, as measured by methods known to those skilled in the art.

As representative second primary solid particles, there may be used aqueous dispersions of nonfilm-forming polymer which are sold under the names "JONCRYL® SCX 8082", "JONCRYL® 90" by the company JOHNSON POLYMER, "NEOCRYL® XK 52" by the company AVECIA RESINS and "RHODOPAS® 5051" by the company RHODIA CHIMIE.

All the constituents present in the composition according to the invention existing in the state of solid particles at 25° C. and which do not coalesce at a temperature of less than or equal to 40° C., on their own or in the presence of the other constituents present in the composition, are considered as being either first solid particles or second solid particles according to the definitions described above.

Thus, for example, the second particles may be made of a material chosen from additional waxes different from the wax described above, fillers, polymers different from the amorphous material present in the second secondary solid particles described above.

The additives described below, when they are in the form of solid particles at 25° C., are considered as being second solid particles described above when these additives possess the corresponding characteristics defined above.

In particular, the adherent polymer present in the composition according to the invention may be in the form of solid particles. In this case, these particles are considered as being solid particles as defined above if this polymer possesses the corresponding characteristics defined above.

In the composition according to the invention, the said first and, where appropriate, the second solid particles are present in an amount such that the volume fraction of the first solid particles and, where appropriate, of the second solid particles is greater than or equal to 50% of the total volume of the nonvolatile fraction of the composition, which means that the total volume of all the first particles and, where appropriate, of the second particles represents at least 50%, such as from 50% to 99%, of the total volume of the nonvolatile fraction of the composition.

The expression "volume fraction of the first solid particles and, where appropriate, of the second solid particles" is understood to mean the percentage total volume of all the first solid particles and, where appropriate, of all the second solid particles present in the nonvolatile fraction of the composition, relative to the total volume of all the compounds of the nonvolatile fraction of the composition.

In one embodiment, the said volume fraction of the first solid particles and, where appropriate, of the second solid particles is greater than or equal to 60%, such as from 60% to 99%, further such as greater than or equal to 70%, or from 70% to 95% of the total volume of the nonvolatile fraction of the composition.

The volume fraction (VF) of solid particles present in the nonvolatile fraction of the composition is equal to the percentage total volume V of the said particles divided by the total volume V' of the nonvolatile fraction of the composition.

The volume V of solid particles is equal to the mass m of the said solid particles in the composition divided by the density d of the particles. The density is calculated according to the method described below.

Volume fraction: $VF = 100 \times V/V'$ and $V = m/d$

The total volume V' of the nonvolatile fraction of the composition can be calculated by adding the volume of each nonvolatile constituent present in the composition.

In one embodiment, when the composition comprises second particles as defined above, the first particles are present in the composition in an amount such that the volume fraction of the first solid particles is greater than or equal to 30% of the total volume fraction of the first and second solid particles, such as from 30% to 100%, further such as greater than or equal to 40%, such as from 40% to 100%, further such as greater than or equal to 50%, such as from 50% to 100%.

In one embodiment, when the composition comprises second primary and/or secondary solid particles as described above, these particles are present in the composition in an amount such that the volume fraction of the said first solid particles and of the said second primary and/or secondary solid particles is greater than or equal to 25.05%, such as from 25.05% to 100%, of the total volume of the first and second solid particles, such as from greater than or equal to 30.05%, further such as from 30.05% to 100%, even further such as greater than or equal to 40.05%, such as from 40.05% to 100%, and even further still greater than or equal to 50.05%, such as from 50.05% to 100%.

As a wax-in-water dispersion, the composition can comprise an aqueous medium forming a continuous aqueous phase.

The composition may also comprise at least one volatile oil and/or one volatile organic solvent such as those described below, which are dispersed in the aqueous phase of the composition.

In the present application, the expression "polymer capable of adhering to the keratinous fibers", called later adherent polymer, is understood to mean a polymer capable of resting attached to keratinous fibers such as the eyelashes, the hair or the skin, during contact of the polymer with the keratinous fibers. In one embodiment, the adherent polymer is capable of forming a deposit on the keratinous fibers and can remain attached to the latter for a normal period of wear.

In one embodiment, the adherent polymer may be a film-forming polymer at a temperature of less than or equal to 40° C. The expression "film-forming polymer" is understood to mean a polymer capable of forming, on its own or in the presence of a film-forming aid, a continuous deposit, such as a film, which adheres to a support, such as to keratinous fibers.

The adherent polymer present in the composition according to the invention may be a polymer solubilized or dispersed in the form of solid particles in an aqueous phase of the composition or alternatively solubilized or dispersed in the form of solid particles in at least one liquid fatty phase. The composition may comprise a mixture of these polymers.

When the film-forming polymer exists in the form of solid particles, these particles may have a mean particle size ranging from 5 nm to 10 μm, such as a mean particle size ranging from 5 nm to 5 μm, such as from 5 nm to 600 nm, and further such as from 20 nm to 300 nm, as measured by methods known to those skilled in the art.

The adherent polymer may be present in the composition according to the invention in a dry matter content ranging from 0.1% to 50% by weight relative to the total weight of the composition, such as from 0.5% to 40% by weight, and further still such as from 1% to 30% by weight.

Representative adherent polymers which can be used in the composition of the present invention include synthetic polymers of the free-radical type or of the polycondensate type, polymers of natural origin and mixtures thereof.

The expression "free-radical polymer" is understood to mean a polymer obtained by polymerization of monomers with ethylenic unsaturation, each monomer being capable of homopolymerizing (in contrast to polycondensates).

The polymers of the free-radical type may be vinyl polymers or copolymers or acrylic polymers.

The vinyl polymers may result from the polymerization of ethylenically unsaturated monomers having at least one acid group and/or esters of these acid monomers and/or amides of these acid monomers.

Representative monomers carrying an acid group include $\alpha,\beta$-ethylenic unsaturated carboxylic acids such as acrylic acid, methacrylic acid, crotonic acid, maleic acid or itaconic acid. (Meth)acrylic acid or crotonic acid can be used.

The esters of acid monomers can be chosen from the esters of acrylic acid and methacrylic acid, also called acrylates or methacrylates, i.e. "(meth)acrylates." In one embodiment, the esters of acid monomers are chosen from alkyl acrylates and alkyl methacrylates, such as $C_1$–$C_{30}$ or $C_1$–$C_{20}$ alkyl acrylates and $C_1$–$C_{30}$ or $C_1$–$C_{20}$ alkyl methacrylates. In another embodiment, the esters of acid monomers are chosen from aryl acrylates and aryl methacrylates, such as $C_6$–$C_{10}$ aryl acrylates and $C_6$–$C_{10}$ aryl methacrylates. In yet another embodiment, the esters of acid monomers are chosen from hydroxyalkyl acrylates and hydroxyalkyl methacrylates, such as $C_2$–$C_6$ hydroxyalkyl acrylates and $C_2$–$C_6$ hydroxyalkyl methacrylates.

Exemplary alkyl (meth)acrylates include methyl methacrylate, ethyl methacrylate, butyl methacrylate, isobutyl methacrylate, 2-ethylhexyl methacrylate, lauryl methacrylate and cyclohexyl methacrylate.

Exemplary hydroxyalkyl (meth)acrylates include hydroxyethyl acrylate, 2-hydroxypropyl acrylate, hydroxyethyl methacrylate and 2-hydroxypropyl methacrylate.

Exemplary aryl (meth)acrylates include benzyl acrylate and phenyl acrylate.

Representative esters of (meth)acrylic acid include alkyl (meth)acrylates.

In on embodiment, the alkyl group of the esters may be either fluorinated or perfluorinated, that is to say that some or all of the hydrogen atoms of the alkyl group are substituted with fluorine atoms.

As amides of the acid monomers, there may be mentioned for example (meth)acrylamides and N-alkyl(meth)acrylamides, such as $C_2$–$C_{12}$ alkyl (meth)acrylamides. Representative N-alkyl(meth)acrylamides include N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. In one embodiment, these monomers may be polymerized with acid monomers and/or their esters and/or their amides, such as those mentioned above.

As examples of vinyl esters, there may be mentioned vinyl acetate, vinyl neodecanoate, vinyl pivalate, vinylbenzoate and vinyl t-butyl benzoate.

As styrene monomers, there may be mentioned styrene and alpha-methylstyrene.

It is possible to use any monomer known to a person skilled in the art entering into the categories of acrylic and vinyl monomers including the monomers modified by a silicone chain.

Representative polycondensates include polyurethanes, polyesters, polyester amides, polyamides, and epoxy ester resins and polyureas.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas, polyurea-polyurethanes and mixtures thereof.

The polyesters may be obtained, in a known manner, by polycondensation of dicarboxylic acids with polyols, such as diols.

The dicarboxylic acid may be aliphatic, alicyclic or aromatic. There may be mentioned as examples of such acids: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecane-dioic acid, 1,3-cyclohexanedicarboxylic acid, 1,4-cyclohexanedicarboxylic acid, isophthalic acid, terephthalic acid, 2,5-norboranedicarboxylic acid, diglycolic acid, thiodipropionic acid, 2,5-naphthalenedicarboxylic acid, and 2,6-naphthalenedicarboxylic acid. These dicarboxylic acid monomers may be used alone or in combination with at least two dicarboxylic acid monomers. Representative dicarboxylic acid monomers include phthalic acid, isophthalic acid, and terephthalic acid.

The diol may be chosen from aliphatic, alicyclic, and aromatic diols. Exemplary diols are chosen from: ethylene glycol, diethylene glycol, triethylene glycol, 1,3-propanediol, cyclohexanedimethanol, and 4-butanediol. Representative polyols include glycerol, pentaerythritol, sorbitol, and trimethylolpropane.

The polyester amides may be obtained in a manner similar to the polyesters, by polycondensation of diacids with diamines or amino alcohols. Exemplary diamines include ethylenediamine, hexamethylenediamine, meta- and para-phenylenediamine. An aminoalcohol, such as monoethanolamine may be used.

The polyester may, in addition, comprise at least one monomer carrying at least one —$SO_3M$ group, where M is chosen from hydrogen, an ammonium ion such as $NH_4^+$ and an alkali, alkaline-earth or metal ion, such as for example an $Na^+$, $Li^+$, $K^+$, $Mg^{2+}$, $Ca^{2+}$, $Cu^{2+}$, $Fe^{2+}$ and $Fe^{3+}$ ion. A bifunctional aromatic monomer comprising such an —$SO_3M$ group may also be used.

The aromatic ring of the bifunctional aromatic monomer carrying, in addition, an —$SO_3M$ group as described above may be chosen for example from benzene, naphthalene, anthracene, diphenyl, oxydiphenyl, sulphonyldiphenyl and methylenediphenyl rings. There may also be mentioned as examples of a bifunctional aromatic monomer carrying, in addition, an —$SO_3M$ group: sulphoisophthalic acid, sulpho-terephthalic acid, sulphophthalic acid, and 4-sulphonaphthalene-2,7-dicarboxylic acid.

Copolymers based on isophthalate/sulphoisophthalate, such as copolymers obtained by condensation of diethylene glycol, cyclohexanedimethanol, isophthalic acid and sulphoisophthalic acid can be used. Such polymers are sold, for example, under the trade name Eastman AQ® by the company Eastman Chemical Products.

The optionally modified polymers of natural origin may be chosen from shellac resin, sandarac gum, dammars, elemis, copals, cellulosic polymers and mixtures thereof.

In one embodiment, the adherent polymer may be present in the form of solid particles in aqueous dispersion in the aqueous medium of the composition, generally known as latex or pseudolatex. The techniques for preparing these dispersions are well known to persons skilled in the art.

Representative aqueous dispersions of film-forming adherent polymer include acrylic dispersions sold under the names NEOCRYL XK-90®, NEOCRYL A-1070®, NEOCRYL A-1090®, NEOCRYL BT-62®, NEOCRYL A-1079®, NEOCRYL A-523® by the company AVECIA-NEORESINS, DOW LATEX 432® by the company DOW CHEMICAL, DAITOSOL 5000 AD® by the company DAITO KASEY KOGYO; or else the aqueous dispersions of polyurethane which are sold under the names NEOREZ R-981®, NEOREZ R-974® by the company AVECIA-NEORESINS, AVALURE UR-405®, AVALURE UR-410®, AVALURE UR-425®, AVALURE UR-450®, SANCURE 875®, SANCURE 861®, SANCURE 878®, SANCURE 2060® by the company GOODRICH, IMPRANIL 85® by the company BAYER, AQUAMERE H-1511® by the company HYDROMER.

Other aqueous dispersions of adherent polymer include dispersions of polymers resulting from the free-radical polymerization of one or more free-radical monomers inside and/or partly at the surface, of preexisting particles of at least one polymer chosen from polyurethanes, polyureas, polyesters, polyesteramides, and/or alkyds. These polymers are generally called hybrid polymers.

In one embodiment, the adherent polymer may be a water-soluble polymer and may be present in the aqueous medium (aqueous phase) of the composition in solubilized form. As examples of water-soluble, in particular film-forming, adherent polymers, there may be mentioned proteins such as proteins of plant origin, such as wheat or soya bean proteins; proteins of animal origin such as keratin, for example keratin hydrolysates and sulphonic keratins;

anionic, cationic, amphoteric or nonionic polymers of chitin or chitosan;

cellulose polymers such as hydroxyethyl cellulose, hydroxypropyl cellulose, methyl cellulose, ethyl hydroxyethyl cellulose, carboxymethyl cellulose, and quaternized derivatives of cellulose;

acrylic polymers or copolymers such as polyacrylates or polymethacrylates;

vinyl polymers, such as polyvinylpyrrolidones, copolymers of methyl vinyl ether and maleic anhydride, the copolymer of vinyl acetate and crotonic acid, copolymers of vinylpyrrolidone and vinyl acetate; copolymers of vinylpyrrolidone and caprolactam; polyvinyl alcohol;

optionally modified polymers of natural origin, such as:
gum arabic, guar gum, xanthan derivatives, karaya gum;
alginates and carrageenans;
glycoaminoglycans, hyaluronic acid and its derivatives;
shellac resin, sandarac gum, dammars, elemis, copals;
deoxyribonucleic acid;
muccopolysaccharides such as hyaluronic acid, chondroitin sulphates, and mixtures thereof.

In one embodiment, the at least one adherent polymer, such as a film forming polymer, may be present in a liquid fatty phase dispersed in the aqueous phase (aqueous medium) of the composition, the liquid fatty phase chosen from oils and organic solvents such as those described above. The expression "liquid fatty phase" is understood to mean, in the context of the invention, a fatty phase which is liquid at room temperature (25° C.) and atmospheric pressure (760 mmHg, that is $10^5$ Pa), comprising one or more fatty substances which are liquid at room temperature, also called oils, which are generally compatible with each other.

In one embodiment, the liquid fatty phase comprises a volatile oil, optionally in the form of a mixture with a nonvolatile oil, it being possible for the oils to be chosen from the oils cited below.

In one embodiment, the at least one adherent, in particular film-forming, polymer may be present in the form of surface-stabilized particles dispersed in the liquid fatty phase.

The dispersion of surface-stabilized polymer particles may be manufactured as described in the document EP-A-749747.

The polymer particles can be surface-stabilized using a stabilizer which may be a block polymer, a graft polymer and/or a random polymer, alone or in the form of a mixture.

Exemplary dispersions of film-forming polymer in the liquid fatty phase, in the presence of stabilizing agents, are described in the documents EP,-A-749746, EP-A-923928, and EP-A-930060, the disclosures of which are specifically incorporated by reference herein.

The size of the polymer particles in dispersion either in the aqueous phase or in the liquid fatty phase may range from 5 nm to 600 nm, such as from 20 nm to 300 nm, as measured by methods known to those skilled in the art In one embodiment, the adherent polymer, such as a film forming polymer, may be solubilized in the liquid fatty phase. In one embodiment, the film-forming polymer can be a fat-soluble polymer.

By way of example of a fat-soluble polymer, there may be mentioned copolymers of vinyl ester (the vinyl group being directly linked to the oxygen atom of the ester group and the vinyl ester having a linear or branched saturated hydrocarbon radical of 1 to 19 carbon atoms, linked to the carbonyl of the ester group) and of at least one other monomer which may be a vinyl ester, different from the vinyl ester already present, an α-olefin, such as a-olefins having from 8 to 28 carbon atoms, an alkyl vinyl ether, such as alkyl vinyl ethers in which the alkyl group comprises from 2 to 18 carbon atoms, or an allyl or methallyl ester such as those esters having a linear or branched saturated hydrocarbon radical of 1 to 19 carbon atoms, linked to the carbonyl of the ester group.

These copolymers may be crosslinked using crosslinking agents which have the aim of which may be either of the vinyl type, or of the allyl or methallyl type, such as tetraallyloxyethane, divinylbenzene, divinyl octanedioate, divinyl dodecanedioate and divinyl octadecanedioate.

As examples of these copolymers, there may be mentioned the copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethyl propionate/vinyl stearate, allyl dimethyl propionate/vinyl stearate, vinyl propionate/vinyl stearate, crosslinked with 0.2% of divinylbenzene, vinyl dimethyl propionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene crosslinked with 0.2% of divinylbenzene, and allyl propionate/allyl stearate crosslinked with 0.2% of divinylbenzene.

Representative fat-soluble polymers include fat-soluble homopolymers, such as those resulting from the homopolymerization of vinyl esters having from 9 to 22 carbon atoms or of alkyl acrylates or methacrylates, the alkyl radicals having from 10 to 20 carbon atoms.

Such fat-soluble homopolymers may be chosen from polyvinyl stearate, polyvinyl stearate crosslinked using divinylbenzene, diallyl ether and diallyl phthalate, polystearyl (meth)acrylate, polyvinyl laurate, and polylauryl (meth) acrylate, it being possible for these poly(meth)acrylates to be crosslinked using ethylene glycol or tetraethylene glycol dimethacrylate.

The fat-soluble copolymers and homopolymers defined above are known and exemplary copolymers and homopolymers are described in application FR-A-2232303; they may have a weight-average molecular weight ranging from 2,000 to 500,000, such as from 4,000 to 200,000.

Representative fat-soluble polymers which can be used in the invention include polyalkylenes such as copolymers of $C_2$–$C_{20}$ alkenes, such as polybutene, alkyl celluloses with a saturated or unsaturated, linear or branched, $C_1$ to $C_8$ alkyl radical such as ethyl cellulose and propyl cellulose, copolymers of vinylpyrrolidone (VP) such as copolymers of vinylpyrrolidone and of a $C_2$ to $C_{40}$ or $C_3$ to $C_{20}$ alkene. By way of example of a VP copolymer which can be used in the invention, there may be mentioned the VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene and VP/acrylic acid/lauryl methacrylate copolymer.

The composition according to the invention may comprise a film-forming aid which promotes the formation of a film with the adherent, in particular film-forming, polymer. Such a film-forming agent may be chosen from all the compounds known to persons skilled in the art to be capable of fulfilling the desired function, and may be chosen from plasticizing agents and coalescing agents.

In one embodiment, the adherent polymer may be a polymer capable of forming a deposit, such as a film, producing, at a concentration of 7% in water, a retraction of isolated stratum corneum of more than 1% at 30° C. under a relative humidity of 40%, such as a retraction of more than 1.2%, and even further of more than 1.5%. This retraction can be measured using an extensiometer, according to the method described below.

The composition according to the invention may comprise, in addition, at least one additional wax different from the hard wax described above.

As additional wax, there may be mentioned in particular beeswax, lanolin wax, Chinese wax, rice wax, Carnauba wax, certain microcrystalline waxes, paraffin waxes, certain ozokerites, certain polyethylene waxes, certain waxes obtained by Fisher-Tropsch synthesis:

There may also be mentioned the waxes obtained by catalytic hydrogenation of animal or vegetable oils having linear or branched $C_8$–$C_{32}$ fatty chains. Among these, there may be mentioned in particular hydrogenated sunflower oil, hydrogenated castor oil, hydrogenated copra oil and hydrogenated lanolin oil. Silicon waxes or fluorinated waxes may also be mentioned.

The additional waxes present in the composition may be dispersed in the form of particles in the aqueous medium of the composition. These particles may have a mean size ranging from 50 nm to 50 µm, such as from 50 nm to 10 µm, as measured by methods known to those skilled in the art.

In particular, the additional waxes are generally present in the composition according to the invention in the form of solid particles and therefore form part of the second solid particles defined above.

The additional wax may be present in the composition according to the invention in an amount ranging from 0.1% to 35% by weight, relative to the total weight of the composition, such as from 0.1% to 20% by weight, and further such as from 1% to 10% by weight.

In one embodiment, the composition may comprise an aqueous medium comprising an aqueous phase, which may be the continuous phase of the composition.

The aqueous medium of the composition forming the aqueous phase may consist essentially of water; or it may also comprise a mixture of water and a water-miscible solvent. A water-miscible solvent is a solvent capable of forming with water a homogeneous mixture transparent to the eye at 25° C. Exemplary water-miscible solvents include lower monoalcohols having from 1 to 5 carbon atoms such as ethanol, isopropanol; glycols having from 2 to 8 carbon atoms such as propylene glycol, ethylene glycol, 1,3-butylene glycol, dipropylene glycol; $C_3$–$C_4$ ketones; and $C_2$–$C_4$ aldehydes.

The aqueous phase (water and optionally the water-miscible organic solvent), or aqueous medium, may be present in an amount ranging from 10% to 95% by weight, relative to the total weight of the composition, such as from 20% to 70% by weight and further such as from 30% to 80% by weight.

In one embodiment, the composition may comprise at least one dispersed volatile organic solvent or oil. The at least one volatile organic solvent or oil may form a fatty phase dispersed in the aqueous phase.

The expression "volatile organic solvent or oil" is understood to mean, in the context of the invention, volatile cosmetic oils and organic solvents, which are liquid at room temperature, having a non-zero vapor pressure, at room temperature and atmospheric pressure, ranging from $10^{-2}$ to 300 mmHg (1.33 Pa to 40 000 Pa) such as a pressure greater than 0.3 mmHg (40 Pa). The expression "nonvolatile oil" is understood to mean an oil having a vapor pressure of less than $10^{-2}$ mmHg (1.33 Pa) at room temperature and atmospheric pressure.

These oils may be hydrocarbon oils, silicone oils, fluorinated oils, or mixtures thereof.

The expression "hydrocarbon oil" is understood to mean an oil containing mainly hydrogen and carbon atoms and optionally oxygen, nitrogen, sulphur and phosphorus atoms. The volatile hydrocarbon oils may be chosen from hydrocarbon oils having from 8 to 16 carbon atoms, for example branched $C_8$–$C_{16}$ alkanes such as $C_8$–$C_{16}$ isoalkanes of petroleum origin (also called isoparaffins) such as isododecane (also called 2,2,4,4,6-pentamethylheptane), isodecane, isohexadecane, and for example the oils sold under the trade names Isopars' or Permetyls, $C_8$–$C_{16}$ branched esters, isohexyl neopentanoate, and mixtures thereof. Other volatile hydrocarbon oils such as petroleum distillates, such as those oils sold under the name Shell Solt by the company SHELL, may also be used. The volatile solvent can be chosen from volatile hydrocarbon oils having from 8 to 16 carbon atoms and mixtures thereof.

Representative volatile oils include volatile silicones, for example volatile linear or cyclic silicone oils, such as those having a viscosity $\leq 8$ centistokes ($8 \times 10^{-6}$ m$^2$/s), and having, for example, from 2 to 7 silicon atoms, these silicones optionally comprising alkyl or alkoxy groups having from 1 to 10 carbon atoms. As volatile silicone oil which can be used in the invention, there may be mentioned octamethylcyclotetrasiloxane, decamethylcyclopentasiloxane, dodecamethylcyclohexa-siloxane, heptamethylhexyltrisiloxane, heptamethyl-octyltrisiloxane, hexamethyidisiloxane, octamethyltri-siloxane, decamethyltetrasiloxane, dodeca methylpenta-siloxane, and mixtures thereof.

The volatile oil or the volatile solvent may be present in the composition according to the invention in an amount ranging from 0.1% to 30% by weight, relative to the total weight of the composition, such as an amount ranging from 0.1% to 15% by weight.

The composition may also comprise at least one nonvolatile oil chosen from nonvolatile hydrocarbon and/or silicone and/or fluorinated oils.

Exemplary nonvolatile hydrocarbon oils include:

hydrocarbon oils of plant origin such as triglycerides, e.g., esters of fatty acids and of glycerol in which the fatty acids may have varying chain lengths from $C_4$ to $C_{24}$, it being possible for the latter to be linear or branched, saturated or unsaturated; exemplary hydrocarbon oils include wheatgerm oil, sunflower oil, grapeseed oil, sesame oil, maize oil, apricot oil, castor oil, karite oil, avocado oil, olive oil, soyabean oil, sweet almond oil, palm oil, rapeseed oil, cottonseed oil, hazelnut oil, macadamia oil, jojoba oil, lucerne oil, poppyseed oil, pumpkinseed oil, sesame oil, gourd oil, rapeseed oil, blackcurrant seed oil, evening primrose oil, millet oil, barley oil, quinoa oil, rye oil, safflower oil, candlenut oil, passionflower oil, rose-muscat oil; or alternatively triglycerides of caprylic/capric acids such as those sold by the company Stearineries Dubois or those sold under the names Miglyol 810, 812 and 818 by the company Dynamit Nobel, synthetic ethers having from 10 to 40 carbon atoms;

linear or branched hydrocarbons of mineral or synthetic origin such as petroleum jelly, polydecenes, hydrogenated polyisobutene such as parleam, squalane, and mixtures thereof;

synthetic esters such as the oils of formula $R_1COOR_2$ in which $R_1$ is a residue of a linear or branched fatty acid comprising from 1 to 40 carbon atoms and $R_2$ is a hydrocarbon chain, such as a branched hydrocarbon chain, containing from 1 to 40 carbon atoms provided that $R_1+R_2$ is $\geq 10$, such as for example Purcellin oil (ketostearyl octanoate), isopropyl myristate, isopropyl palmitate, $C_{12}$ to $C_{15}$ alcohol benzoate, hexyl laurate, diisopropyl adipate, isononyl isononanoate, 2-ethylhexyl palmitate, isostearyl isostearate, octanoates, decanoates or ricinoleates of alcohols or of polyalcohols such as propylene glycol dioctanoate; hydroxylated esters such as isostearyl lactate, diisostearyl malate; and esters of pentaerythritol;

fatty alcohols which are liquid at room temperature containing a branched and/or unsaturated carbon chain having from 12 to 26 carbon atoms such as octyl dodecanol, isostearyl alcohol, oleyl alcohol, 2-hexyldecanol, 2-butyloctanol, 2-undecylpentadecanol;

higher fatty acids such as oleic acid, linoleic acid, linolenic acid; and mixtures thereof.

The nonvolatile silicone oils which can be used in the composition according to the invention may be nonvolatile polydimethylsiloxanes (PDMS), polydimethylsiloxanes comprising alkyl or alkoxy groups, pendant and/or at the silicone chain end, groups each having from 2 to 24 carbon atoms, phenylated silicones such as phenyltrimethicones, phenyldimethicones, phenyltrimethylsiloxydi-phenylsiloxanes, diphenyldimethicones, diphenylmethyl-d iphenyltrisiloxanes, and (2-phenylethyl)trimethylsioloxy-silicates.

The fluorinated oils which can be used in the invention include fluorosilicone oils, fluorinated polyethers, fluorinated silicones, such as those as described in the document EP-A-847752.

The nonvolatile oils may be present in the composition according to the invention in an amount ranging from 0.1% to 30% by weight, such as from 0.1% to 15% by weight, relative to the total weight of the composition.

In one embodiment, when the composition comprises a volatile oil and a nonvolatile oil, the amount of volatile oil and of volatile oil in the composition can be less than or equal to 49% by weight, relative to the total weight of the composition, such as an amount less than 25% by weight, and even further such as still less than 15% by weight.

The composition according to the invention may contain at least one surfactant, such as emulsifying surfactants. The at least one surfactant may be present in an amount ranging from 2 to 30% by weight relative to the total weight of the composition, such as from 5% to 15%. The at least one surfactant may be chosen from anionic and nonanionic surfactants. Reference may be made to the document "Encyclopedia of Chemical Technology, KIRK-OTHMER", volume 22, p. 333–432, $3^{rd}$ edition, 1979, WILEY, for the definition of the properties and functions (emulsifier) of the surfactants, for example p. 347–377 of this reference, for anionic and nonionic surfactants.

Exemplary surfactants used in the composition according to the invention may be chosen from:

nonionic surfactants: fatty acids, fatty alcohols, polyethoxylated or polyglycerolated fatty alcohols such as polyethoxylated stearyl or cetylstearyl alcohols, esters of fatty acid and of sucrose, esters of alkyl glucose, such as polyoxyethylenated fatty esters of $C_1$–$C_6$ alkyl glucose, and mixtures thereof;

anionic surfactants: $C_{16}$–$C_{30}$ fatty acids neutralized with amines, aqueous ammonia or alkaline salts and mixtures thereof; oxyethylenated acrylic acid/monostearyl itaconate copolymer (20 EO) as an aqueous dispersion at 30% by weight sold under the name "STRUCTURE 2001" by the company National Starch, ethoxylated acrylic acid/monocetyl itaconate copolymer (20 EO) as an aqueous dispersion at 30% sold under the name "STRUCTURE 3001" by the company National Starch.

In one embodiment, the at least one surfactant allows the production of an oil-in-water or wax-in-water emulsion.

The composition according to the invention may also comprise a coloring substance such as pulverulent coloring substances, fat-soluble colorants, water-soluble colorants. This coloring substance may be present in an amount ranging from 0.01% to 50% by weight, relative to the total weight of the composition, such as from 0.01% to 30% by weight.

The pulverulent coloring substances may be chosen from pigments and pearlescent agents.

The pigments may be white or colored, inorganic and/or organic, coated or otherwise. Representative inorganic pigments include titanium dioxide, optionally surface-treated, zirconium, zinc or cerium oxides, as well as iron or chromium oxides, manganese violet, ultramarine blue, chromium hydrate and ferric blue. Representative organic pigments include carbon black, pigments of the D & C type, and lacquers based on carmine, barium, strontium, calcium or aluminium.

The pearlescent agents may be chosen from white pearlescent pigments such as mica coated with titanium or bismuth oxychloride, colored pearlescent pigments such as mica-titanium with iron oxides, mica-titanium with ferric blue or chromium oxide, mica-titanium with an organic pigment of the abovementioned type as well as pearlescent pigments based on bismuth oxychloride.

The fat-soluble colorants include, for example, Sudan red, D&C Red 17, D&C Green 6, β-carotene, soyabean oil, Sudan brown, D&C Yellow 11, D&C Violet 2, D&C Orange 5, quinoline yellow, annatto. The water-soluble colorants include, for example, sugarbeet juice and methylene blue.

The composition of the invention may comprise, in addition, any additive conventionally used in cosmetics, such as antioxidants, fillers, preservatives, perfumes, neutralizing agents, thickeners, cosmetic or dermatological active agents such as, for example, emollients, moisturizers, vitamins, sunscreens, and mixtures thereof. These additives may be present in the composition in an amount ranging from 0.01 to 20% of the total weight of the composition, such as from 0.01 to 10% (if present).

Of course persons skilled in the art will be careful to choose the possible additional additives and/or their quantity such that the advantageous properties of the composition according to the invention are not or not substantially impaired by the addition envisaged.

The composition according to the invention may be manufactured by known methods which are generally used in the cosmetic or dermatological field.

Method of Measuring the Density of Solid Particles:

The apparent density of solid particles is measured using a Gay-Lussac pycnometer.

A precision scale (precision of 1 mg) is used and the measurements are carried out in a thermostatic chamber at 25° C. (±0.5° C.). Two reference liquids having a density d, which are demineralized water (d=1 000 kg/m³) and heptane (d=683.7 kg/m³) are also used. The density of the solid particles is measured with each reference liquid.

The pycnometer and the products used for carrying out the measurement are placed at the temperature of 25° C. The masses cited below are expressed in kilograms.

The mass M0 of the pycnometer is measured, then the pycnometer is completely filled with the reference liquid used, avoiding introducing air bubbles. The mass M1 of the filled pycnometer is measured.

A mixture of mass M2 of the material whose density d2 it is desired to measure with a mass M3 of reference liquid is then prepared. The mixture is stirred and then just before the end of stirring, the pycnometer is filled with this mixture and the mass M4 of the filled pycnometer is measured. The mass M4−M0 of the mixture present in the pycnometer is thus measured.

The pycnometer having a constant filling volume, it is therefore possible to establish the following relationship:

$$(M1-M0)/d=(M2/d2+M3/d) \times (M4-M0)/(M2+M3)$$

This relationship makes it possible to calculate the value of the density d2 of the solid particles, expressed in kg/m³. A value of the density of the solid particles is thus determined for each of the reference liquids. The highest value (among the density measured with distilled water and the density measured with heptane) is selected as value of the density for the determination of the volume fraction of the solid particles.

Method for Measuring Retraction of a Polymer:

The length of a test piece of isolated stratum corneum is measured before treatment and after treatment, followed by determining the percentage retraction of the test piece.

Test pieces of 1 cm×0.4 cm of stratum corneum are used which have a thickness ranging from 10 to 20 μm placed on the extensiometer MTT 610 marketed by the company DIASTRON.

The test piece is placed between 2 jaws and left for 12 hours in an atmosphere at 30° C. and 40% relative humidity.

The test piece is drawn, at the rate of 2 mm/minute, by a length of between 5 and 10% of the initial length in order to determine the length $l_1$ from which the test piece begins to exert a force on the jaws and which is detected by the apparatus.

The test piece is then relaxed and then 2 mg of an aqueous composition containing 7% by weight of polymer are applied to the stratum corneum. After evaporation of the composition, the test piece is drawn under the same conditions as those described above in order to also determine the length $l_2$ for the treated test piece.

The percentage retraction is determined by the ratio: $100 \times (l_2 - l_1)/l_1$.

The invention is illustrated in greater detail in the following examples.

COMPARATIVE EXAMPLES 1 and 2 a) There were prepared 2 aqueous wax dispersions, one (dispersion 1) with the wax sold under the name "PHYTO-WAX Olive 18 L 57" by the company SOPHIM (wax having a hardness equal to 10.05 MPa), the other (dispersion 2) with beeswax (wax having a hardness equal to 3.68 MPa).

Each wax dispersion is prepared by mixing, at 95° C., 40 g of wax, 4 g of polyoxyethylenated lauryl alcohol surfactant containing 23 ethylene oxide units sold under the name "BRIJ 35" by the company UNICHEMA and 56 g of water heated to 95° C., with stirring using an Ultraturrax stirrer, until an aqueous wax dispersion having a mean particle size of about 300 nm is obtained.

b) There were prepared 2 mascaras having the following composition:

| | |
|---|---|
| Wax | 30 g |
| Black iron oxide (Sicovit black 85E172 from BASF) | 5 g |
| Hydroxyethylcellulose (Cellosize QP4400M from Amerchol) | 1 g |
| Propylene glycol | 5 g |
| Surfactant (Brij 35) | 7.5 g |
| Water | qs 100 g |

The mascara according to the invention (Example 1) contains the wax sold under the name "PHYTOWAX Olive 18 L 57" by the company SOPHIM of the dispersion 1.

The mascara not forming part of the invention (Example 2) contains the beeswax of the dispersion 2.

Each mascara is prepared by mixing 75 g of the corresponding wax dispersion described in point a) above with the complementary aqueous fraction comprising the other ingredients.

The nonvolatile fraction of these 2 mascaras contains a volume fraction of solid particles (wax, black iron oxide) of 84% (relative to the total volume of the nonvolatile fraction).

In the mascara of Example 1, the volume fraction of the hard wax represents 96.8% of the total volume of the solid particles. The mascara of Example 2 does not contain hard wax.

The curling properties of these 2 mascaras were measured according to the following protocol:

Test pieces of Caucasian hair comprising 15 hair strands of 15 mm in length having an arc of curvature having a radius of curvature of between 6 and 7 mm, were used. These test pieces are attached to a support such that the top of the test piece corresponds to the inner side of the arc formed by the test piece, the bottom of the test piece corresponding to the outer side of the arc formed by the test piece.

Before applying the mascara, the curvature of the hair test piece was measured by taking a digital profile photo using Macrozoom Navitar.

The mascara is then applied to each test piece using a brush over the bottom of the test piece. There were carried out 3 series of 10 passages of the brush with a waiting time of 2 minutes between each series of 10 passages.

20 minutes after the last passage of the brush over the test piece, the test piece of hair with make-up is photographed.

The images are processed with the Microvision image analysing system and the mean radius of curvature of the hair strands before make-up application (Rci) and the mean radius of curvature of the hair after make-up application (Rcf) are measured, the radius of curvature being measured in millimeters.

The curling R is calculated according to the formula:

$R = 1/Rci - 1/Rcf$

The higher the value of R, the greater the curling of the eyelashes which is measured.

The following results were obtained:

Example 1 (invention): $R = 0.018$ mm$^{-1}$

Example 2 (outside invention): $R = 0.012$ mm$^{-1}$

It was thus observed that the curling properties of the mascara of Example 1 according to the invention are superior to those of the mascara of Example 2. The use of a harder wax present in the mascara of Example 1 makes it possible to increase the curling of the eyelashes.

What is claimed is:

1. A composition for coating keratinous fibers comprising a wax-in-water dispersion comprising, in a cosmetically acceptable aqueous medium, a nonvolatile fraction comprising:

at least one polymer capable of adhering to the keratinous fibers, and first particles which are solid at 25° C. comprising a first material comprising at least one wax having a melting point of less than 77° C. and a hardness greater than or equal to 6.5 MPa, and optionally second solid particles comprising a second material different from the first material, the second solid particles not being capable of coalescing at a temperature of less than or equal to 40° C., wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition, and, where appropriate, the volume fraction of the first solid particles is greater than or equal to 25% of the total volume of the first solid particles and of the second solid particles.

2. The composition according to claim 1, wherein the keratinous fibers are eyelashes.

3. The composition according to claim 1, wherein the at least one wax has a melting point of less than 60° C.

4. The composition according to claim 3, wherein the at least one wax has a melting point ranging from 30° C. to 59° C.

5. The composition according to claim 4, wherein the at least one wax has a melting point ranging from 35° C. to 59° C.

6. The composition according to claim 5, wherein the at least one wax has a melting point ranging from 40° C. to 50° C.

7. The composition according to claim 1, wherein the at least one wax has a hardness ranging from 6.5 MPa to 20 MPa.

8. The composition according to claim 7, wherein the at least one wax has a hardness ranging from 6.5 MPa to 15 MPa.

9. The composition according to claim 8, wherein the at least one wax has a hardness ranging from 6.5 to 12 MPa.

10. The composition according to claim 9, wherein the at least one wax has a hardness ranging from 9.7 to 20 MPa.

11. The composition according to claim 10, wherein the at least one wax has a hardness ranging from 9.7 to 15 MPa.

12. The composition according to claim 11, wherein the at least one wax has a hardness ranging from 9.7 to 12 to MPa.

13. The composition according to claim 1, wherein the at least one wax is chosen from Candelilla wax, hydrogenated jojoba wax, sumac wax, ceresin, octacosanyl stearate, tetracontanyl stearate, Shellac wax, behenyl-fumarate, di(1,1,1-trimethylolpropane) tetrastearate, di(1,1,1-trimethylolpropane) tetrabehenate, ozokerites, waxes obtained by hydrogenation of olive oil esterified with stearyl alcohol, and waxes obtained by hydrogenation of castor oil esterified with cetyl alcohol.

14. The composition according to claim 1, wherein the at least one wax is chosen from di(1,1,1-trimethylolpropane) tetrastearate and olive waxes obtained by hydrogenation of olive oil esterified with stearyl alcohol.

15. The composition according to claim 1, wherein the first particles have a mean size ranging from 50 nm to 50 µm.

16. The composition according to claim 1, wherein the first particles have a mean size ranging from 100 nm to 10 µm.

17. The composition according to claim 1, wherein the first particles are present in the composition in an amount ranging from 1.25% to 50% by weight, relative to the total weight of the composition.

18. The composition according to claim 17, wherein the first particles are present in the composition in an amount ranging from 5% to 40% by weight, relative to the total weight of the composition.

19. The composition according to claim 18, wherein the first particles are present in the composition in an amount ranging from 10% to 25% by weight, relative to the total weight of the composition.

20. The composition according to claim 1, wherein the composition comprises the first particles and the second solid particles.

21. The composition according to claim 1, wherein the volume fraction of the first particles and, where appropriate, of the second solid particles is greater than or equal to 60% of the total volume of the nonvolatile fraction of the composition.

22. The composition according to claim 21, wherein the volume fraction of the first particles and, where appropriate, of the second solid particles is greater than or equal to 70% of the total volume of the nonvolatile fraction of the composition.

23. The composition according to claim 1, wherein the second solid particles are chosen from:
second primary solid particles, comprising a first material chosen from crystalline and semicrystalline materials, the first material being solid at 25° C. exhibiting at least one of a first order phase transition, a melting transition, and a combustion transition, greater than 100° C.;
second secondary solid particles, comprising at least one amorphous material having a glass transition temperature of greater than or equal to 60° C.,
second tertiary solid particles which are solid at 25° C., wherein the second tertiary solid particles are different from the said second primary and secondary particles and mixtures thereof.

24. The composition according to claim 23, wherein the first material has a first order phase transition greater than 120° C.

25. The composition according to claim 24, wherein the first material has a first order phase transition greater than 150° C.

26. The composition according to claim 25, wherein the first material has a Vicker hardness greater than or equal to 10.

27. The composition according to claim 26, wherein the first material has a Vicker hardness ranging from 10 to 7,500.

28. The composition according to claim 26, wherein the first material has a Vicker hardness greater than or equal to 200.

29. The composition according to claim 28, wherein the first material has a Vicker hardness ranging from 200 to 7,500.

30. The composition according to claim 26, wherein the first material has a Vicker hardness greater than or equal to 400.

31. The composition according to claim 30, wherein the first material has a Vicker hardness ranging from 400 to 7,500.

32. The composition according to claim 23, wherein the first material is chosen from silica, glass, diamond, copper, boron nitride, ceramics, micas, metal oxides, polyamides, and mixtures thereof.

33. The Composition according to claim 32, wherein the metal oxides are chosen from iron oxides.

34. The composition according to claim 23, wherein the second primary particles have a mean size ranging from 50 nm to 50 µm.

35. The composition according to claim 34, wherein the second primary particles have a mean size ranging from 20 nm to 50 µm.

36. The composition according to claim 23, wherein the at least one amorphous material has a glass transition temperature greater than or equal to 80° C.

37. The composition according to claim 36, the at least one amorphous material has a glass transition temperature greater than or equal to 100° C.

38. The composition according to claim 23, wherein the at least one amorphous material is chosen from polymers.

39. The composition according to claim 23, wherein the at least one amorphous material is chosen from polymers chosen from free-radical polymers and polycondensates.

40. The composition according to claim 23, wherein the at least one amorphous material is chosen from polymers chosen from ethylene polymers, propylene polymers, acrylic polymers, acrylamide polymers, acrylonitrile polymers, methacrylonitrile polymers, polycarbonates, polyurethanes, polyesters, polyamides, polysulphones, polysulphonamides, and carbohydrates.

41. The composition according to claim 23, wherein the second secondary solid particles have a mean size ranging from 10 nm to 50 μm.

42. The composition according to claim 41, wherein the second secondary solid particles have a mean size ranging from 20 nm to 1 μm.

43. The composition according to claim 1, wherein the volume fraction of the first solid particles, and, where appropriate, of the second solid particles ranges from 50% to 99% of the total volume of the nonvolatile fraction of the composition.

44. The composition according to claim 1, wherein the volume fraction of the first solid particles, and, where appropriate, of the second solid particles is greater than or equal to 60%, of the total volume of the nonvolatile fraction of the composition.

45. The composition according to claim 44, wherein the volume fraction of the first solid particles, and, where appropriate, of the second solid particles ranges from 60% to 99%, of the total volume of the nonvolatile fraction of the composition.

46. The composition according to claim 44, wherein the volume fraction of the first solid particles, and, where appropriate, of the second solid particles is greater than or equal to 70%, of the total volume of the nonvolatile fraction of the composition.

47. The composition according to claim 46, wherein the volume fraction of the first solid particles, and, where appropriate, of the second solid particles ranges from 70% to 95%, of the total volume of the nonvolatile fraction of the composition.

48. The composition according to claim 1, wherein the first particles are present in the composition in an amount such that the volume fraction of the first solid particles is greater than or equal to 30%, of the total volume fraction of the first and second solid particles.

49. The composition according to claim 48, wherein the first particles are present in the composition in an amount such that the volume fraction of the first solid particles ranges from 30% to 100%, of the total volume fraction of the first and second solid particles.

50. The composition according to claim 48, wherein the first particles are present in the composition in an amount such that the volume fraction of the first solid particles is greater than or equal to 40%, of the total volume fraction of the first and second solid particles.

51. The composition according to claim 50, wherein the first particles are present in the composition in an amount such that the volume fraction of the first solid particles ranges from 40% to 100%, of the total volume fraction of the first and second solid particles.

52. The composition according to claim 48, wherein the first particles are present in the composition in an amount such that the volume fraction of the first solid particles is greater than or equal to 50%, of the total volume fraction of the first and second solid particles.

53. The composition according to claim 52, wherein the first particles are present in the composition in an amount such that the volume fraction of the first solid particles ranges from 50% to 100%, of the total volume fraction of the first and second solid particles.

54. The composition according to claim 23, wherein the second primary and/or secondary solid particles are present in the composition in an amount such that the volume fraction of said first solid particles and of the said second primary and/or secondary solid particles, is greater than or equal to 25.05%, of the total volume of the first and second solid particles.

55. The composition according to claim 54, wherein the second primary and/or secondary solid particles are present in the composition in an amount such that the volume fraction of said first solid particles and of the said second primary and/or secondary solid particles, from 25.05% to 100%, of the total volume of the first and second solid particles.

56. The composition according to claim 54, wherein the second primary and/or secondary solid particles are present in the composition in an amount such that the volume fraction of said first solid particles and of the said second primary and/or secondary solid particles is greater than or equal to 30.05%, of the total volume of the first and second solid particles.

57. The composition according to claim 56, wherein the second primary and/or secondary solid particles are present in the composition in an amount such that the volume fraction of said first solid particles and of the said second primary and/or secondary solid particles ranges from 30.05% to 100%, of the total volume of the first and second solid particles.

58. The composition according to claim 54, wherein the second primary and/or secondary solid particles are present in the composition in an amount such that the volume fraction of said first solid particles and of the said second primary and/or secondary solid particles is greater than or equal to 40.05%, of the total volume of the first and second solid particles.

59. The composition according to claim 58, wherein the second primary and/or secondary solid particles are present in the composition in an amount such that the volume fraction of said first solid particles and of the said second primary and/or secondary solid particles ranges from 40.05% to 100%, of the total volume of the first and second solid particles.

60. The composition according to claim 54, wherein the second primary and/or secondary solid particles are present in the composition in an amount such that the volume fraction of said first solid particles and of the said second primary and/or secondary solid particles is greater than or equal to 50.05%, of the total volume of the first and second solid particles.

61. The composition according to claim 60, wherein the second primary and/or secondary solid particles are present in the composition in an amount such that the volume fraction of said first solid particles and of the said second primary and/or secondary solid particles ranges from 50.05% to 100%, of the total volume of the first and second solid particles.

62. The composition according to claim 1, wherein the at least one polymer capable of adhering to the keratinous fibers is chosen from vinyl polymers, polyurethanes, polyesters, polyamides, polyureas, and cellulose polymers.

63. The composition according to claim 1, wherein the at least one polymer capable of adhering to the keratinous fibers is a film-forming polymer at a temperature of less than or equal to 40° C.

64. The composition according to claim 1, wherein the at least one polymer capable of adhering to the keratinous fibers is capable of forming a deposit producing, at a concentration of 7% in water, a retraction of the isolated stratum corneum of more than 1% at 30° C. at a relative humidity of 40%.

65. The composition according to claim 64, wherein the retraction of the stratum corneum is more than 1.2%.

66. The composition according to claim 64, wherein the retraction of the stratum corneum is more than 1.5%.

67. The composition according to claim 1, wherein the at least one polymer capable of adhering to the keratinous fibers is solubilized in the aqueous medium.

68. The composition according to claim 1, wherein the at least one polymer capable of adhering to the keratinous fibers is in the form of solid particles in aqueous dispersion.

69. The composition according to claim 1, wherein the at least one polymer capable of adhering to the keratinous fibers is solubilized or dispersed in the form of surface-stabilized particles in at least one liquid fatty phase dispersed in the aqueous medium.

70. The composition according to claim 1, wherein the at least one polymer capable of adhering to the keratinous fibers is present in an amount ranging from 0.1% to 50% by weight, relative to the total weight of the composition.

71. The composition according to claim 70, wherein the at least one polymer capable of adhering to the keratinous fibers is present in an amount ranging from 0.5% to 40% by weight, relative to the total weight of the composition.

72. The composition according to claim 71, wherein the at least one polymer capable of adhering to the keratinous fibers is present in an amount ranging from 1% to 30% by weight, relative to the total weight of the composition.

73. The composition according to claim 1, further comprising at least one additional wax different from the wax of the first solid particles.

74. The composition according to claim 73, wherein the at least one additional wax is present in the composition in an amount ranging from 0.1% to 35% by weight, relative to the total weight of the composition.

75. The composition according to claim 74, wherein the at least one additional wax is present in the composition in an amount ranging from 0.1% to 20% by weight, relative to the total weight of the composition.

76. The composition according to claim 75, wherein the at least one additional wax is present in the composition in an amount ranging from 1% to 10% by weight, relative to the total weight of the composition.

77. The composition according to claim 73, wherein the at least one additional wax is in the form of particles having a mean size ranging from 50 nm to 50 μm.

78. The composition according to claim 77, wherein the at least one additional wax is in the form of particles having a mean size ranging from 50 nm to 10 μm.

79. The composition according to claim 1, wherein the aqueous medium is chosen from water, and a mixture of water and at least one water-miscible organic solvent.

80. The composition according to claim 79, wherein the at least one water-miscible organic solvent is chosen from lower monoalcohols having from 1 to 5 carbon atoms, glycols having from 2 to 8 carbon atoms, $C_3$–$C_4$ ketones, and $C_2$–$C_4$ aldehydes.

81. The composition according to claim 1, wherein the aqueous medium is present in an amount ranging from 10% to 95% by weight, relative to the total weight of the composition.

82. The composition according to claim 81, wherein the aqueous medium is present in an amount ranging from 20% to 70% by weight, relative to the total weight of the composition.

83. The composition according to claim 82, wherein the aqueous medium is present in an amount ranging from 30% to 80% by weight, relative to the total weight of the composition.

84. The composition according to claim 1, further comprising at least one additive chosen from volatile oils and volatile organic solvents.

85. The composition according to claim 84, wherein the volatile oils are chosen from hydrocarbon oils, silicone oils, and fluorinated oils.

86. The composition according to claim 84, wherein the volatile oils are present in an amount ranging from 0.1% to 30% by weight, relative to the total weight of the composition.

87. The composition according to claim 84, wherein the volatile oils are present in an amount ranging from 0.1% to 15% by weight, relative to the total weight of the composition.

88. The composition according to claim 1, further comprising at least one nonvolatile oil.

89. The composition according to claim 88, wherein the at least one nonvolatile oil is present in an amount ranging from 0.1% to 50% by weight, relative to the total weight of the composition.

90. The composition according to claim 89, wherein the at least one nonvolatile oil is present in an amount ranging from 0.1% to 30% by weight, relative to the total weight of the composition.

91. The composition according to claim 1, further comprising at least one surfactant.

92. The composition according to claim 1, further comprising at least one additive chosen from colouring substances, antioxidants, fillers, preservatives, perfumes, neutralizing agents, thickeners, cosmetic active agents, sunscreens, coalescing agents, and plasticizers.

93. A mascara comprising composition comprising a wax-in-water dispersion comprising, in a cosmetically acceptable aqueous medium, a nonvolatile fraction comprising:
at least one polymer capable of adhering to the keratinous fibers, and
first particles which are solid at 25° C. comprising a first material comprising at least one wax having a melting point of less than 77° C. and a hardness greater than or equal to 6.5 MPa,
and optionally second solid particles comprising a second material different from the first material, the second solid particles not being capable of coalescing at a temperature of less than or equal to 40° C.,
wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition,
and, where appropriate, the volume fraction of the first solid particles is greater than or equal to 25% of the total volume of the first solid particles and of the second solid particles.

94. A method of applying make-up to or for a nontherapeutic treatment of keratinous fibers, comprising:
applying to the keratinous fibers, a composition comprising a wax-in-water dispersion comprising, in a cosmetically acceptable aqueous medium, a nonvolatile fraction comprising:
at least one polymer capable of adhering to the keratinous fibers, and
first particles which are solid at 25° C. comprising a first material comprising at least one wax having a melting point of less than 77° C. and a hardness greater than or equal to 6.5 MPa,
and optionally second solid particles comprising a second material different from the first material, the second solid particles not being capable of coalescing at a temperature of less than or equal to 40° C.,
wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition,
and, where appropriate, the volume fraction of the first solid particles is greater than or equal to 25% of the total volume of the first solid particles and of the second solid particles.

95. The method according to claim 94, wherein the keratinous fibers are eyelashes.

96. A method for curling keratinous fibers, comprising:
applying to the keratinous fibers in an amount effective to curl the keratinous fibers, a composition comprising a wax-in-water dispersion comprising, in a cosmetically acceptable aqueous medium, a nonvolatile fraction comprising:
at least one polymer capable of adhering to the keratinous fibers, and
first particles which are solid at 25° C. comprising a first material comprising at least one wax having a melting point of less than 77° C. and a hardness greater than or equal to 6.5 MPa,
and optionally second solid particles comprising a second material different from the first material, the second solid particles not being capable of coalescing at a temperature of less than or equal to 40° C.,
wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition,
and, where appropriate, the volume fraction of the first solid particles is greater than or equal to 25% of the total volume of the first solid particles and of the second solid particles.

97. A method for improving the curling capability of a composition for coating keratinous fibers, the composition comprising a wax-in-water dispersion comprising, in a cosmetically acceptable aqueous medium, a nonvolatile fraction comprising at least one polymer capable of adhering to keratinous fibers, the method comprising:
adding to the non-volatile fraction,
first particles which are solid at 25° C. comprising a first material comprising at least one wax having a melting point of less than 77° C. and a hardness of greater than or equal to 6.5 MPa,
and optionally second solid particles comprising a second material different from the first material, the second solid particles not being capable of coalescing at a temperature of less than or equal to 40° C.,
wherein the first solid particles and, where appropriate, the second solid particles are present in the composition in an amount such that the volume fraction of the first solid particles and, where appropriate, of the second solid particles is greater than or equal to 50% of the total volume of the nonvolatile fraction of the composition,
and, where appropriate, the volume fraction of the first solid particles is greater than or equal to 25% of the total volume of the first solid particles and of the second solid particles.

98. The method according to claim 97, wherein the keratinous fibers are eyelashes.

99. A composition for coating keratinous fibers comprising a wax-in-water dispersion comprising, in a cosmetically acceptable aqueous medium, a nonvolatile fraction comprising:
first particles which are solid at 25° C. comprising a first material comprising at least one wax having a melting point of less than 77° C. and a hardness greater than or equal to 6.5 MPa,
and optionally second solid particles comprising a second material different from the first material, the second solid particles not being capable of coalescing at a temperature of less than or equal to 40° C.,
wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition,
and, where appropriate, the volume fraction of the first solid particles is greater than or equal to 25% of the total volume of the first solid particles and of the second solid particles, and wherein at least a portion of at least one of said first particles and said optional second solid particles are chosen from at least one polymer capable of adhering to the keratinous fibers.

* * * * *

UNITED STATES PATENT AND TRADEMARK OFFICE
CERTIFICATE OF CORRECTION

PATENT NO. : 7,029,662 B2 Page 1 of 1
APPLICATION NO. : 10/195419
DATED : April 18, 2006
INVENTOR(S) : Auguste et al.

It is certified that error appears in the above-identified patent and that said Letters Patent is hereby corrected as shown below:

In claim 12, column 19, line 31, "12 to MPa." should read --12 MPa.--.

In claim 13, column 19, line 35, "behenyl-fumarate," should read --behenyl fumarate,--.

In claim 33, column 20, line 52, "Composition" should read --composition--.

In claim 37, column 20, line 63, "36, the" should read --36, wherein the--.

In claim 55, column 22, line 17, "particles, from" should read --particles ranges from--.

Signed and Sealed this

Fifteenth Day of August, 2006

JON W. DUDAS
*Director of the United States Patent and Trademark Office*